(12) United States Patent
Murata et al.

(10) Patent No.: US 6,479,705 B2
(45) Date of Patent: Nov. 12, 2002

(54) PROCESS FOR PREPARING KETONE, ALCOHOL AND HYDROPEROXIDE

(75) Inventors: Shuzo Murata, Niihama (JP); Nobuhiro Tani, Niihama (JP); Hiroyuki Asano, Niihama (JP)

(73) Assignees: Sumitomo Chemical Company, Limited, Osaka (JP); Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/735,926

(22) Filed: Dec. 14, 2000

(65) Prior Publication Data

US 2001/0016670 A1 Aug. 23, 2001

(30) Foreign Application Priority Data

Dec. 14, 1999 (JP) .......................... 11-354216

(51) Int. Cl.⁷ .......................... C07C 45/29; C07C 37/00
(52) U.S. Cl. .................. 568/320; 568/357; 568/389; 568/802
(58) Field of Search ................. 568/320, 357, 568/389, 802

(56) References Cited

U.S. PATENT DOCUMENTS

| 5,780,683 A | 7/1998 | Greene et al. | 568/358 |
| 5,958,821 A | 9/1999 | Ishii et al. | 502/167 |
| 5,981,420 A | 11/1999 | Nakano et al. | 502/155 |

FOREIGN PATENT DOCUMENTS

| EP | 0 858 835 A1 | 8/1998 | B01J/31/02 |
| JP | 1-102035 | 4/1989 | C07C/27/12 |
| JP | 8-38909 | 2/1996 | B01J/31/06 |
| JP | 9-202742 | 8/1997 | C07C/27/12 |
| JP | 11-349493 | 12/1999 | C07B/33/00 |

OTHER PUBLICATIONS

European Search Report.
Chemical Abstract No. 1997:424747.
Chemical Abstract No. 1997:358592.
Chemical Abstract No. 1996:265125.
Iwahama, Takahiro et al, "Direct Conversion of Cyclohexane into Adipic with Molecular Oxygen Catalyzed by N–Hydroxyphthalimide Combined with Mn(acac)$_2$ and Co(Oac)$_2$", Organic Process Research & Development, 1998, vol. 2, No. 4, pp. 255–260.
Patent Abstract of JP 11–349493 (1999).
Patent Abstract of JP 8–038909 (1996).
Patent Abstract of JP 9–202742 (1997).
Patent Abstract of JP 1–102035 (1989).

*Primary Examiner*—Sreeni Padmanabhan
*Assistant Examiner*—Sikarl A. Witherspoon
(74) *Attorney, Agent, or Firm*—Sughrue Mion, PLLC

(57) ABSTRACT

A process for preparing a ketone, an alcohol and/or a hydroperoxide is provided by reacting a hydrocarbon with molecular oxygen in the presence of a cyclic N-hydroxyimide and a compound of a transition metal, in which an oxygen-containing gas is supplied in a reaction system and at the same time a gas containing 1 to-about 8.59, by volume of oxygen is discharged from the reaction system. This process is excellent in productivity and safety and produces the desired products at a high selectivity.

2 Claims, No Drawings

PROCESS FOR PREPARING KETONE, ALCOHOL AND HYDROPEROXIDE

BACKGROUND OF THE INVENTION

1. Field of the Invention

The present invention relates to a process for preparing a ketone, an alcohol and a hydroperoxide. In particular, the present invention relates to a process for preparing a ketone, an alcohol and a hydroperoxide comprising allowing a hydrocarbon to be in contact with molecular oxygen to obtain a corresponding ketone, alcohol and/or hydroperoxide.

2. Background Art

Hitherto, it is known to obtain a ketone, an alcohol and/or a hydroperoxide by allowing a corresponding hydrocarbon to be in contact with molecular oxygen (hereinafter referred to as "oxygen" simply) to oxidize the hydrocarbon. For example, a process for preparing a KA oil (a mixture of cyclohexanone and cyclohexanol) by oxidizing cyclohexane with oxygen and a process for preparing a phenylalkyl hydroperoxide by oxidizing an alkylbenzene with oxygen are known.

In these years, a process has been developed, which comprises oxidizing a hydrocarbon with oxygen in the presence of a catalyst which comprises an imide compound such as N-hydroxyphthalimide, or a catalyst which comprises such an imide compound and a metal compound. For example, JP-A-8-38909 discloses a process comprising oxidizing various hydrocarbons with oxygen in an organic solvent using the above-described catalyst. JP-A-9-87215 discloses a process comprising oxidizing cyclohexane with passing an air or a mixture of nitrogen and oxygen using the above-described catalyst in the absence of a solvent.

However, the process disclosed in JP-A-8-38909 is not satisfactory, since their volume efficiency is low and thus the productivity is insufficient, and furthermore the safety of the process is not satisfactory, and the process disclosed in JP-A-9-87215 is not satisfactory either, since a reaction rate is low and thus the productivity is insufficient.

SUMMARY OF THE INVENTION

One object of the present invention is to provide a process for preparing a ketone, an alcohol and/or a hydroperoxide with a high selectivity by oxidizing a corresponding hydrocarbon with oxygen, which is excellent in productivity and safety.

As a result of the extensive study by the inventors, it has been found that the above object can be achieved when a hydrocarbon is oxidized with oxygen in the presence of a cyclic N-hydroxyimide and a compound of a transition metal while supplying an oxygen-containing gas in a reaction system and discharging a gas having a specific oxygen concentration from the reaction system, and thus the present invention has been completed.

Accordingly, the present invention provides a process for preparing at least one compound selected from the group consisting of a ketone, an alcohol and a hydroperoxide comprising the step of reacting a hydrocarbon with molecular oxygen in the presence of a cyclic N-hydroxyimide and a compound of a transition metal, wherein an oxygen-containing gas is supplied in a reaction system and at the same time a gas containing about 1 to about 10% by volume of oxygen is discharged from the reaction system.

DETAILED DESCRIPTION OF THE INVENTION

According to the present invention, the ketone, alcohol and/or hydroperoxide are prepared by oxidizing the hydrocarbon with molecular oxygen in the presence of the cyclic N-hydroxyimide and the compound of the transition metal. In the course of the reaction, the oxygen-containing gas is supplied in the reaction system and at the same time the gas containing about 1 to about 10% by volume of oxygen is discharged from the reaction system.

Examples of the hydrocarbon used in the present invention include saturated alicyclic hydrocarbons (e.g. cyclopentane, cyclohexane, methylcyclohexane, adamantane, etc.), unsaturated alicyclic hydrocarbons (e.g. cyclopentene, cyclohexene, methylcyclohexene, cyclopentadiene, etc.), aromatic hydrocarbons (e.g. toluene, xylene, cumene, cymene, diisopropylbenzene, tetrahydronaphthalene (Tetraline), indane, etc.), and the like. Among them, the saturated alicyclic hydrocarbons are preferable.

As a result of the oxidation of the hydrocarbon, a compound corresponding to the hydrocarbon in which two hydrogen atoms of the methylene group are substituted with oxo groups is obtained as a ketone, a compound corresponding to the hydrocarbon in which a hydrogen atom of the methyl group, the methylene group or the metylidyne group is substituted with a hydroxyl group is obtained as an alcohol. Furthermore, a compound corresponding to the hydrocarbon in which a hydrogen atom of the methyl group, the methylene group or the metylidyne group is substituted with a hydroperoxy group as an hydroperoxide. For example, when a cycloalkane is used as the hydrocarbon, a cycloalkanone, a cycloalkanol and/or a cycloalkyl hydroperoxide can be obtained.

In the present invention, a combination of the cyclic N-hydroxyimide and the compound of the transition metal is used as a catalyst for the reaction of the hydrocarbon and oxygen.

Examples of the cyclic N-hydroxyimide include N-hydroxyphthalimide, N-hydroxynaphthalimide, N-hydroxymaleimide, N-hydroxysuccnineimide, whichmayhave a substituent, andthe like. Examples of the substituent include an alkyl group, an aryl group, a halogen atom, a nitro group, etc. Specific examples of the cyclic N-hycroxyimide include N-hydroxyphthalimide, N-hydroxychlorophthalimide, N-hydroxynitrophthalmimide, N-hydroxynaphthalimide, N-hydroxychloronaphthalimide, N-hydroxymaleimide, N-hydroxysuccnineimide, etc. The cyclic N-hydroxyimides may be used independently or as a mixture of two or more.

The amount of the cyclic N-hydroxyimide may be from 0.0001 to 20 mole %, preferably from 0.001 to 10 mole %, based on the hydrocarbon.

Examples of the transition metal contained in the compound of the transition metal include cerium, titanium, vanadium, chromium, molybdenum, manganese, iron, ruthenium, cobalt, rhodium, nickel, copper, etc. Among them, cobalt, cerium and manganese are preferable.

Examples of the compound of the transition metal include oxides, organic acid salts, inorganic acid salts, halides, alkoxides, complexes such as acetylacetonate, oxoacids and their salts, isopolyacids and their salts, heteropolyacids and their salts, etc. The transition metals may be used in combination of two or more of them.

The amount of the compound of the transition metal used may be from 0.00001 to 1 mole %, preferably from 0.0001 to 0.5 mole %, based on the hydrocarbon.

In the process of the present invention, the reaction may be carried out in the presence of a solvent. Examples of the solvent include nitriles (e.g. benzonitrile, acetonitrile, etc.), organic acids (e.g. formic acid, acetic acid, etc.), nitro compounds (e.g. nitromethane, nitrobenzene, etc.), chlorohydrocarbons (e.g. chlorobenzene, 1,2-dichloroethane, etc.), and mixtures thereof. When the solvent is used, an amount thereof may be at least about 0.01 part by weight, preferably at least about 0.05 part by weight, and may be about 4 parts by weight or less, preferably about 1.5 parts by weight or less, per one part by weight of the hydrocarbon.

In the process of the present invention, the oxygen-containing gas is supplied in the reaction system containing the hydrocarbon, the catalyst, the optional solvent, etc., and at the same time, the gas is discharged from the reaction system.

As the oxygen-containing gas supplied, oxygen gas, an air, or oxygen gas or an air, each of which is diluted with an inert gas such as nitrogen gas or helium gas may be used.

The concentration of the oxygen in the oxygen-containing gas may be at least 2% by volume, preferably at lest 5% by volume from the viewpoint of the reaction rate, and may not exceed 30% by volume, preferably 25% by volume from the viewpoint of the safety.

The supply rate of the oxygen-containing gas may be from 0.001 to 1 mole/hr., preferably from 0.01 to 0.5 mole/hr. in terms of the oxygen, per one mole of the hydrocarbon.

The oxygen-containing gas may be supplied in the reaction system such that the bubbles of the oxygen-containing gas are. dispersed in the mixture containing the hydrocarbon and the catalyst. The oxygen-containing gas may be supplied with a gas-inlet tube or through a nozzle provided in a reactor.

The size of the bubbles is appropriately selected. The bubble size may be made small, preferably to 1 mm or less, from the viewpoint of the increase of the reaction rate.

The concentration of the oxygen in the gas discharged from the reaction system may be from about 1 to about 10% by volume, preferably from about 1 to about 8.5% by volume. Preferably, the average concentration of the oxygen in the gas discharged during the reaction is in the above range. More preferably, the concentration of the oxygen in the gas discharged during the reaction is always substantially in the above range.

When the concentration of the oxygen in the gas discharged is less than about 1% by volume, the selectivity to the desired product such as the ketone, the alcohol or the hydroperoxide is insufficient. When this concentration exceeds about 10% by volume, the selectivity to the desired product is insufficient, and such a high concentration of the oxygen is undesirable from the viewpoint of the costs and the safety of the process.

The concentration of the oxygen can be adjusted by the suitable selection of the kind and amount of the catalyst, the supply rate and oxygen concentration of the oxygen-containing gas supplied, the reaction temperature, the reaction time, the reaction pressure, etc.

The ratio of the oxygen concentration in the gas discharged to that in the oxygen-containing gas supplied is preferably from about 0.04 to about 0.9.

In the course of the reaction, one or both of the supply and discharge of the gas may be carried out discontinuously or continuously, if desired. Preferably, the gas is continuously supplied under a constant pressure, and the gas is continuously discharged to maintain such a pressure.

The reaction temperature maybe from about 70 to about 200° C., preferably from 75 to 150° C., and the reaction pressure may be from about 0.1 to 3 MPa, preferably from 0.1 to 2 MPa. In the process of the present invention, the reaction may be carried out batchwise or continuously. The reaction can be carried out continuously by supplying the hydrocarbon and the catalyst and at the same time discharging the reaction mixture while supplying and discharging the gas. Thereby, the operability and productivity of the process can be much increased.

A method of post-treatment of the reaction mixture after the reaction may be suitably selected depending on the properties of the products, etc. Examples of the post-treatment are filtration, concentration, washing, alkali-treatment, acid-treatment, etc. Two or more of these post-treatments may be combined, if necessary. The alkali-treatment can regenerate the alcohol by saponifying an ester of the alcohol with a carboxylic acid as a by-product, and also convert the hydroperoxide to the ketone or the alcohol.

To purify the product, distillation or crystallization can be used.

As described above, according. to the present invention, the ketone, alcohol and/or hydroperoxide can be prepared from the corresponding hydrocarbon with, a high selectivity thereto by the process which is excellent in the productivity and safety.

EXAMPLES

The present invention will be illustrated by the following Examples, which do not limit the scope of the invention in any way.

In the Examples and Comparative Examples, each oxygen-containing gas having a given oxygen concentration was prepared by diluting the air with nitrogen gas.

When the oxygen-containing gas was bubbled, a gas-inlet tube was utilized. In Examples 1 to 11 and Comparative Examples 1 and 2, a glass filter was attached at the tip end of the gas-inlet tube so that the bubble size was 1 mm or less.

The gas was discharged via a condenser and a pressure-reserve valve, and water maintained at 8° C. was used as a coolant for the condenser.

The analysis of cyclohexane, cyclohexanone, cyclohexanol and cyclohexyl hydroperoxide was carried out with gas chromatography, and the analysis of adipic acid was carried out with ion chromatography. The conversion of cyclohexane and the selectivities to the products were calculated from the results of these analyses.

Example 1

In a one liter glass autoclave, cyclohexane (84 g, 1 mole), N-hydroxyphthalimide (0.1 mole), cobalt(II) acetate tetrahydrate (0.001 mole) and acetonitrile (110 g) were charged, and a pressure and a temperature were adjusted at 0.6 MPa and 75° C., respectively, under a nitrogen atmosphere. Through the mixture in the autoclave, an oxygen-containing gas having an oxygen concentration of 9.3% by volume was bubbled at a flow rate of 450 ml/min. for 6 hours while stirring and maintaining the above pressure and temperature. From the time when the start of the oxygen gas absorption was detected (after one hour from the start of the gas bubbling) to the end of the gas bubbling, an average oxygen. concentration in the gas discharged was 4.6% by volume.

According to the analyses of the reaction mixture, the conversion of cyclohexane was 35.1%, and the selectivities to cyclohexanone, cyclohexanol and cyclohexyl hydroperoxide were 57.2%, 5.4% and 2.0%, respectively (the total selectivity: 64.6%).

Example 2

In a one liter glass autoclave, cyclohexane (84 g, 1 mole), N-hydroxyphthalimide (0.1 mole), cobalt(II) acetate tetrahydrate (0.001 mole) and acetonitrile (110 g) were charged, and a pressure and a temperature were adjusted at 1.05 MPa and 75° C., respectively, under a nitrogen atmosphere. Through the mixture in the autoclave, an oxygen-containing gas having an oxygen concentration of 10.5% by volume was bubbled at a flow rate of 500 ml/min. for 4 hours while stirring and maintaining the above pressure and temperature. From the time when the start of the oxygen gas absorption was detected (after one hour from the start of the gas bubbling) to the end of the gas bubbling, an average oxygen concentration in the gas discharged was 6.9% by volume.

According to the analyses of the reaction mixture, the conversion of cyclohexane was 25.5%, and the selectivities to cyclohexanone, cyclohexanol and cyclohexyl hydroperoxide were 64.5%, 6.6% and 1.6%, respectively (the total selectivity: 72.7%). The selectivity to adipic acid was 7.5%.

Example 3

In a one liter glass autoclave, cyclohexane (84 g, 1 mole), N-hydroxyphthalimide (0.1 mole), cobalt (II) acetate tetrahydrate (0.001 mole) and acetonitrile (110 g) were charged, and a pressure and a temperature were adjusted at 1.05 MPa and 75° C., respectively, under a nitrogen atmosphere. Through the mixture in the autoclave, an oxygen-containing gas having an oxygen concentration of 10.5% by volume was bubbled at a flow rate of 500 ml/min. for 5 hours while stirring and maintaining the above pressure and temperature. From the time when the start of the oxygen gas absorption was detected (after 0.7 hour from the start of the gas bubbling) to the end of the gas bubbling, an average oxygen concentration in the gas discharged was 5.4% by volume.

According to the analyses of the reaction mixture, the conversion of cyclohexane was 34.0%, and the selectivities to cyclohexanone and cyclohexanol were 70.8% and 9.6%, respectively (the total selectivity: 80.4%)

Example 4

In a one liter glass autoclave, cyclohexane (84 g, 1 mole), N-hydroxyphthalimide (0.1 mole), cobalt(II) acetate tetrahydrate (0.0005 mole) and acetonitrile (110 g) were charged, and a pressure and a temperature were adjusted at 1.05 MPa and 75° C., respectively, under a nitrogen atmosphere. Through the mixture in the autoclave, an oxygen-containing gas having an oxygen concentration of 10.5% by volume was bubbled at a flow rate of 500 ml/min. for 6 hours while stirring and maintaining the above pressure and temperature. From the time when the start of the oxygen gas absorption was detected (after one hour from the start of the gas bubbling) to the end of the gas bubbling, an average oxygen concentration in the gas discharged was 8.4% by volume.

According to the analyses of the reaction mixture, the conversion of cyclohexane was 23.6%, and the selectivities to cyclohexanone, cyclohexanol and cyclohexyl hydroperoxide were 58.8%, less than 0.1% and 16.7%, respectively (the total selectivity: 75.5%). The selectivity to adipic acid was 8.1%.

Example 5

In a one liter glass autoclave, cyclohexane (84 g, 1 mole), N-hydroxyphthalimide (0.1 mole), cobalt(II) acetate tetrahydrate (0.0005 mole) and acetonitrile (110 g) were charged, and a pressure and a temperature were adjusted at 1.05 MPa and 85° C., respectively, under a nitrogen atmosphere. Through the mixture in the autoclave, an oxygen-containing gas having an oxygen concentration of 10.5% by volume was bubbled at a flow rate of 500 ml/min. for 3 hours while stirring and maintaining the above pressure and temperature. From the time when the start of the oxygen gas absorption was detected (after 30 minutes from the start of the gas bubbling) to the end of the gas bubbling, an average oxygen concentration in the gas discharged was 2.9% by volume.

According to the analyses of the reaction mixture, the conversion of cyclohexane was 26.1%, and the selectivities to cyclohexanone, cyclohexanol and cyclohexyl hydroperoxide were 58.3%, 9.2% and 7.2%, respectively (the total selectivity: 74.7%). The selectivity to adipic acid was 6.9%.

Example 6

In a one liter glass autoclave, cyclohexane (84 g, 1 mole), N-hydroxyphthalimide (0.1 mole), cobalt (II) acetate tetrahydrate (0.0005 mole) and acetonitrile (110 g) were charged, and a pressure and a temperature were adjusted at 1.05 MPa and 95° C., respectively, under a nitrogen atmosphere. Through the mixture in the autoclave, an oxygen-containing gas having an oxygen concentration of 10.5% by volume was bubbled at a flow rate of 500 ml/min. for 2 hours while stirring and maintaining the above pressure and temperature. From the time when the start of the oxygen gas absorption was detected (after one hour from the start of the gas bubbling) to the end of the gas bubbling, an average oxygen concentration in the gas discharged was 1.3% by volume.

According to the analyses of the reaction mixture, the conversion of cyclohexane was 22.8%, and the selectivities to cyclohexanone, cyclohexanol and cyclohexyl hydroperoxide were 58.5%, 10.8% and 7.2%, respectively (the total selectivity: 76.5%). The selectivity to adipic acid was 4.3%.

Example 7

In a one liter glass autoclave, cyclohexane (168 g, 2 moles), N-hydroxyphthalimide (0.13 mole), cobalt(II) acetate tetrahydrate (0.0007 mole) and acetonitrile (91 g) were charged, and a pressure and a temperature were adjusted at 1.05 MPa and 100° C., respectively, under a nitrogen atmosphere. Through the mixture in the autoclave, an oxygen-containing gas having an oxygen concentration of 18.8% by volume was bubbled at a flow rate of 500 ml/min. for 2.5 hours while stirring and maintaining the above pressure and temperature. From the time when the start of the oxygen gas absorption was detected (after 0.2 hour from the start of the gas bubbling) to the end of the gas bubbling, an average oxygen concentration in the gas discharged was 5.6% by volume.

According to the analyses of the reaction mixture, the conversion of cyclohexane was 16.4%, and the selectivities to cyclohexanone, cyclohexanol and cyclohexyl hydroperoxide were 58.0%, 4.5% and 15.8%, respectively (the total selectivity: 78.3%). The selectivity to adipic acid was 8.1%.

Example 8

In a one liter glass autoclave, cyclohexane (84 g, 1 mole), N-hydroxyphthalimide (0.1 mole), cerium(II) acetate (0.001 mole) and acetonitrile (110 g) were charged, and a pressure and a temperature were adjusted at 1.05 MPa and 100° C., respectively, under a nitrogen atmosphere. Through the mixture in the autoclave, an oxygen-containing gas having an oxygen concentration of 6.3% by volume was bubbled at a flow rate of 500 ml/min. for 11 hours while stirring and maintaining the above pressure and temperature. From the time when the start of the oxygen gas absorption was detected (after 3 hours from the start of the gas bubbling) to the end of the gas bubbling, an average oxygen concentration in the gas discharged was 2.8% by volume.

According to the analyses of the reaction mixture, the conversion of cyclohexane was 19.3%, and the selectivities to cyclohexanone, cyclohexanol and cyclohexyl hydroperoxide were 29.6%, less than 0.1% and 54.4%, respectively (the total selectivity: 84.0%). The selectivity to adipic acid was 5.7%.

Example 9

In a one liter glass autoclave, cyclohexane (126 g, 1.5 moles), N-hydroxyphthalimide (0.098 mole), manganese (III) acetylacetonate (0.0005 mole) and acetonitrile (66 g) were charged, and a pressure and a temperature were adjusted at 1.05 MPa and 100° C., respectively, under a nitrogen atmosphere. Through the mixture in the autoclave, an oxygen-containing gas having an oxygen concentration of 6.3% by volume was bubbled at a flow rate of 500 ml/min. for 8 hours while stirring and maintaining the above pressure and temperature. From the time when the start of the oxygen gas absorption was detected (after 2 hours from the start of the gas bubbling) to the end of the gas bubbling, an average oxygen concentration in the gas discharged was 5.1% by volume.

According to the analyses of the reaction mixture, the conversion of cyclohexane was 14.5%, and the selectivities to cyclohexanone, cyclohexanol and cyclohexyl hydroperoxide were 32.3%, less than 0.1% and 51.9%, respectively (the total selectivity: 84.2%). The selectivity to adipic acid was 7.9%.

Example 10

In a one liter glass autoclave, cyclohexane (126 g, 1.5 moles), N-hydroxyphthalimide (0.098 mole), manganese (III) acetylacetonate (0.0005 mole), cobalt (II) acetate tetrahydrate (0.00005 mole) and acetonitrile (66 g) were charged, and a pressure and a temperature were adjusted at 1.05 MPa and 100° C., respectively, under a nitrogen atmosphere. Through the mixture in the autoclave, an oxygen-containing gas having an oxygen concentration of 10.5% by volume was bubbled at a flow rate of 500 ml/min. for 7.3 hours while stirring and maintaining the above pressure and temperature. From the time when the start of the oxygen gas absorption was detected (after 1.3 hours from the start of the gas bubbling) to the end of the gas bubbling, an average oxygen concentration in the gas discharged was 3.2% by volume.

According to the analyses of the reaction mixture, the conversion of cyclohexane was 8.1%, and the selectivities to cyclohexanone, cyclohexanol and cyclohexyl hydroperoxide were 39.6%, 5.8% and 40.7%, respectively (the total selectivity: 86.1%). The selectivity to adipic acid was 2.8%.

Example 11

In a one liter glass autoclave, cyclohexane (84 g, 1 mole), N-hydroxyphthalimide (0.1 mole), titanium(IV) tetraisopropoxide (0.0001 mole), cobalt(II) acetate tetrahydrate (0.0001 mole) and acetonitrile (110 g) were charged, and a pressure and a temperature were adjusted at 1.05 MPa and 100° C., respectively, under a nitrogen atmosphere. Through the mixture in the autoclave, an oxygen-containing gas having an oxygen concentration of 12.5% by volume was bubbled at a flow rate of 500 ml/min. for 6 hours while stirring and maintaining the above pressure and temperature. From the time when the start of the oxygen gas absorption was detected (after 30 minutes from the start of the gas bubbling) to the end of the gas bubbling, an average oxygen concentration in the gas discharged was 7.1% by volume.

According to the analyses of the reaction mixture, the conversion of cyclohexane was 24.0%, and the selectivities to cyclohexanone, cyclohexanol and cyclohexyl hydroperoxide were 66.6%, less than 0.1% and 13.0%, respectively (the total selectivity: 79.6%). The selectivity to adipic acid was 10.7%.

Example 12

In a one liter glass autoclave, cyclohexane (126 g, 1.5 moles), N-hydroxyphthalimide (0.02 mole), cobalt(II) octylate (0.0002 mole) and acetonitrile (182 g) were charged, and a pressure and a temperature were adjusted at 1.05 MPa and 80° C., respectively, under a nitrogen atmosphere. Through the mixture in the autoclave, an oxygen-containing gas having an oxygen concentration of 8.7% by volume was bubbled at a flow rate of 340 ml/min. while maintaining the above pressure and temperature. After one hour from the start of the gas bubbling, the supply of a 445 wt. ppm solution of cobalt octylate in cyclohexane and a 1.7 wt.% solution of N-hydroxyphthalimide in acetonitrile was started at a flow rate of 0.5 g/min. and 0.7 g/min., respectively while bubbling the gas. Successively, the reaction mixture was discharged at substantially the same rate as the supply rate while maintaining the above pressure and temperature, and the reaction was continued for 8 hours at a residence time of 4 hours. An average oxygen concentration in the gas discharged was 5.0% by volume.

According to the analyses of the reaction mixture, the conversion of cyclohexane was 8.3%, and the selectivities to cyclohexanone, cyclohexanol and cyclohexyl hydroperoxide were 56.5%, 1.9% and 25.3%, respectively (the total selectivity: 83.7%). The selectivity to adipic acid was 8.8%.

Comparative Example 1

In a one liter glass autoclave, cyclohexane (84 g, 1 mole), N-hydroxyphthalimide (0.1 mole), cobalt(II) acetate tetrahydrate (0.001 mole) and acetonitrile (110 g) were charged, and a pressure and a temperature were adjusted at 0.6 MPa and 75° C., respectively, under a nitrogen atmosphere. Through the mixture in the autoclave, an air (an oxygen concentration of 21% by volume) was bubbled at a flow rate of 60 ml/min. for 6 hours while stirring and maintaining the above pressure and temperature. From the time when the start of the oxygen gas absorption was detected (after 0.7 hour from the start of the gas bubbling) to the end of the gas bubbling, an average oxygen concentration in the gas discharged was 0.7% by volume.

According to the analyses of the reaction mixture, the conversion of cyclohexane was 25.1%, and the selectivities to cyclohexanone, cyclohexanol and cyclohexyl hydroperoxide were 44.1%, 3.8% and 5.3%, respectively (the total selectivity: 53.2%)

Comparative Example 2

In a one liter glass autoclave, cyclohexane (84 g, 1 mole), N-hydroxyphthalimide (0.1 mole), cobalt(II) acetate tetrahydrate (0.001 mole) and acetonitrile (110 g) were charged, and a pressure and a temperature were adjusted at 0.6 MPa and 75° C., respectively, under a nitrogen atmosphere. Through the mixture in the autoclave, an oxygen-containing gas having an oxygen concentration of 5% by volume was bubbled at a flow rate of 490 ml/min. for 6 hours while stirring and maintaining the above pressure and temperature. From the time when the start of the oxygen gas absorption was detected (after 0.8 hour from the start of the gas bubbling) to the end of the gas bubbling, an average oxygen concentration in the gas discharged was 0.8% by volume.

According to the analyses of the reaction mixture, the conversion of cyclohexane was 36.9%, and the selectivities to cyclohexanone, cyclohexanol and cyclohexyl hydroperoxide were 43.7%, 4.2% and 1.6%, respectively (the total selectivity: 49.5%).

Comparative Example 3

In a 110 ml stainless steel autoclave in which a glass inner tube was inserted, cyclohexane (23.5 g, 0.28 mole), N-hydroxyphthalimide (0.028 mole), cobalt(II) acetate tetrahydrate (0.00028 mole) and acetonitrile (31 g) were charged, and the mixture was stirred at a temperature of 75° C. under an oxygen atmosphere of a pressure of 0.26 MPa for 7 hours.

According to the analyses of the reaction mixture, the conversion of cyclohexane was 30.3%, and the selectivities to cyclohexanone, cyclohexanol and cyclohexyl hydroperoxide were 48.9%, less than 0.1% and 7.5%, respectively (the total selectivity: 56.4%). The selectivity to adipic acid was 20.4%.

What is claimed is:

1. A process for preparing at least one compound selected from the group consisting of a ketone, an alcohol and a hydroperoxide comprising the step of reacting a hydrocarbon with molecular oxygen in the presence of a cyclic N-hydroxyimide and a compound of a transition metal, wherein as oxygen-containing gas is supplied in a reaction system and at the same time a gas containing about 1 to about 8.5% by volume of oxygen is discharged from the reaction system.

2. The process according to claim 1, wherein said hydrocarbon is a saturated alicyclic hydrocarbon.

* * * * *